United States Patent
Cige et al.

(10) Patent No.: US 11,896,736 B2
(45) Date of Patent: Feb. 13, 2024

(54) BIOMATERIAL IMPLANTS AND METHODS OF MAKING THE SAME

(71) Applicant: GLOBUS MEDICAL, INC., Audubon, PA (US)

(72) Inventors: Joshua Cige, Conshohocken, PA (US); Archana Bhat, Phoenixville, PA (US); Joanna Marquez, San Antonio, TX (US)

(73) Assignee: Globus Medical, Inc, Audubon, PA (US)

( * ) Notice: Subject to any disclaimer, the term of this patent is extended or adjusted under 35 U.S.C. 154(b) by 847 days.

(21) Appl. No.: 16/926,905

(22) Filed: Jul. 13, 2020

(65) Prior Publication Data

US 2022/0008615 A1  Jan. 13, 2022

(51) Int. Cl.
*A61L 27/36* (2006.01)
*A61L 27/56* (2006.01)

(52) U.S. Cl.
CPC ......... *A61L 27/3608* (2013.01); *A61L 27/365* (2013.01); *A61L 27/3616* (2013.01); *A61L 27/3683* (2013.01); *A61L 27/56* (2013.01); *A61L 2430/02* (2013.01); *A61L 2430/40* (2013.01)

(58) Field of Classification Search
CPC .......... A61F 2/06; A61F 2/07; A61L 27/3608; A61L 27/3676; A61L 27/365; A61L 27/3683

See application file for complete search history.

(56) References Cited

U.S. PATENT DOCUMENTS

| | | |
|---|---|---|
| 4,437,191 A | 3/1984 | van der Zel et al. |
| 5,231,169 A | 7/1993 | Constantz |
| 5,507,813 A | 4/1996 | Dowd et al. |
| 5,510,396 A | 4/1996 | Prewett et al. |
| 5,556,430 A | 9/1996 | Gendler |
| 5,681,872 A | 10/1997 | Erbe |
| 5,700,289 A | 12/1997 | Breitbart et al. |
| 5,707,962 A | 1/1998 | Chen et al. |
| 5,776,193 A | 7/1998 | Kwan et al. |
| 5,854,207 A | 12/1998 | Lee et al. |
| 5,914,356 A | 6/1999 | Erbe |
| 5,939,039 A | 8/1999 | Sapieszko et al. |
| 6,030,635 A | 2/2000 | Gertzman et al. |
| 6,123,731 A | 9/2000 | Boyce et al. |
| 6,180,606 B1 | 1/2001 | Chen et al. |
| 6,264,701 B1 | 7/2001 | Brekke |
| 6,294,041 B1 | 9/2001 | Boyce et al. |
| 6,309,659 B1 | 10/2001 | Clokie |
| 6,350,283 B1 | 2/2002 | Michelson |
| 6,372,257 B1 | 4/2002 | Marchosky |

(Continued)

FOREIGN PATENT DOCUMENTS

| | | |
|---|---|---|
| CA | 1341610 C | 4/1989 |
| CA | 2027259 C | 12/2000 |

(Continued)

*Primary Examiner* — Jason-Dennis N Stewart (57) ABSTRACT

Biomaterials, implants made therefrom, methods of making the biomaterial and implants, methods of promoting bone or wound healing in a mammal by administering the biomaterial or implant to the mammal, and kits that include such biomaterials, implants, or components thereof. The biomaterials may include demineralized cortical fibers, which help to promote bone repair.

20 Claims, 4 Drawing Sheets

(56) References Cited

U.S. PATENT DOCUMENTS

| | | |
|---|---|---|
| 6,432,436 B1 | 8/2002 | Gertzman et al. |
| 6,436,138 B1 | 8/2002 | Dowd et al. |
| 6,437,018 B1 | 8/2002 | Gertzman et al. |
| 6,458,375 B1 | 10/2002 | Gertzman et al. |
| 6,478,825 B1 | 11/2002 | Winterbottom et al. |
| 6,548,080 B1 | 4/2003 | Gertzman et al. |
| 6,666,890 B2 | 12/2003 | Michelson |
| 6,696,073 B2 | 2/2004 | Boyce et al. |
| 6,706,067 B2 | 3/2004 | Shimp et al. |
| 6,723,131 B2 | 4/2004 | Muschler |
| 6,749,636 B2 | 6/2004 | Michelson |
| 6,752,831 B2 | 6/2004 | Sybert et al. |
| 6,776,800 B2 | 8/2004 | Boyer, II et al. |
| 6,808,585 B2 | 10/2004 | Boyce et al. |
| 6,843,807 B1 | 1/2005 | Boyce et al. |
| 6,919,308 B2 | 7/2005 | Oppermann et al. |
| 6,949,251 B2 | 9/2005 | Dalal et al. |
| 7,022,137 B2 | 4/2006 | Michelson |
| 7,041,641 B2 | 5/2006 | Rueger et al. |
| 7,132,110 B2 | 11/2006 | Kay et al. |
| 7,156,880 B2 | 1/2007 | Evans et al. |
| 7,166,133 B2 | 1/2007 | Evans et al. |
| 7,175,858 B2 | 2/2007 | Constantz et al. |
| 7,235,107 B2 | 6/2007 | Evans et al. |
| 7,262,003 B2 | 8/2007 | Kumar et al. |
| 7,275,933 B2 | 10/2007 | Jia et al. |
| 7,291,345 B2 | 11/2007 | Winterbottom et al. |
| 7,332,452 B2 | 2/2008 | Ogawa et al. |
| 7,390,498 B2 | 6/2008 | Dalal et al. |
| 7,393,405 B2 | 7/2008 | Bohner |
| 7,473,678 B2 | 1/2009 | Lynch |
| 7,494,950 B2 | 2/2009 | Armitage et al. |
| 7,498,041 B2 | 3/2009 | Masinaei et al. |
| 7,517,489 B2 | 4/2009 | Akash |
| 7,537,617 B2 | 5/2009 | Bindsell et al. |
| 7,582,309 B2 | 9/2009 | Rosenberg et al. |
| 7,611,536 B2 | 11/2009 | Michelson |
| 7,723,395 B2 | 5/2010 | Ringeisen et al. |
| 7,744,597 B2 | 6/2010 | Gaskins et al. |
| 7,776,100 B2 | 8/2010 | Brekke et al. |
| 7,785,634 B2 | 8/2010 | Borden |
| 7,811,608 B2 | 10/2010 | Kay et al. |
| 7,824,702 B2 | 11/2010 | Wironen et al. |
| 7,833,278 B2 | 11/2010 | Evans et al. |
| 7,887,598 B2 | 2/2011 | Evans et al. |
| 7,892,291 B2 | 2/2011 | Evans et al. |
| 7,910,690 B2 | 3/2011 | Ringeisen et al. |
| 7,931,692 B2 | 4/2011 | Sybert et al. |
| 7,939,108 B2 | 5/2011 | Morris et al. |
| 7,942,961 B2 | 5/2011 | Asgarg |
| 7,947,759 B2 | 5/2011 | Lin et al. |
| 7,959,941 B2 | 6/2011 | Knaack et al. |
| 7,977,094 B2 | 7/2011 | Masinaei et al. |
| 8,002,813 B2 | 8/2011 | Scarborough et al. |
| 8,067,078 B1 | 11/2011 | Espinosa et al. |
| 8,093,313 B2 | 1/2012 | Miller |
| 8,105,383 B2 | 1/2012 | Michelson |
| 8,137,403 B2 | 3/2012 | Michelson |
| 8,147,860 B2 | 4/2012 | Rosenberg et al. |
| 8,147,862 B2 | 4/2012 | McKay |
| 8,163,032 B2 | 4/2012 | Evans et al. |
| 8,188,229 B2 | 5/2012 | Ringeison et al. |
| 8,197,474 B2 | 6/2012 | Scarborough et al. |
| 8,202,539 B2 | 6/2012 | Behnam et al. |
| 8,221,781 B2 | 7/2012 | Rosenberg et al. |
| 8,232,327 B2 | 7/2012 | Garigapati et al. |
| 8,268,008 B2 | 9/2012 | Betz et al. |
| 8,287,915 B2 | 10/2012 | Clineff et al. |
| 8,303,967 B2 | 11/2012 | Clineff et al. |
| 8,303,971 B2 | 11/2012 | Cieslik et al. |
| 8,309,106 B2 | 11/2012 | Masinaei et al. |
| 8,323,700 B2 | 12/2012 | Morris et al. |
| 8,328,876 B2 | 12/2012 | Behnam et al. |
| 8,333,985 B2 | 12/2012 | Knaack et al. |
| 8,357,384 B2 | 1/2013 | Behnam et al. |
| 8,394,141 B2 | 3/2013 | Mills et al. |
| 8,399,409 B2 | 3/2013 | Lynch et al. |
| 8,419,802 B2 | 4/2013 | Evans et al. |
| 8,425,619 B2 | 4/2013 | Evans et al. |
| 8,435,306 B2 | 5/2013 | Evans et al. |
| 8,435,343 B2 | 5/2013 | Yahav et al. |
| 8,435,566 B2 | 5/2013 | Behnam et al. |
| 8,454,988 B2 | 6/2013 | Rosenberg et al. |
| 8,460,686 B2 | 6/2013 | Clineff et al. |
| 8,475,824 B2 | 7/2013 | McKay |
| 8,506,981 B1 | 8/2013 | Borden |
| 8,506,985 B2 | 8/2013 | Garcia De Castro Andrews et al. |
| 8,524,265 B2 | 9/2013 | McKay |
| 8,529,962 B2 | 9/2013 | Morris et al. |
| 8,545,858 B2 | 10/2013 | Rosenberg et al. |
| 8,545,864 B2 | 10/2013 | Morris et al. |
| 8,551,519 B2 | 10/2013 | Bezwada |
| 8,551,525 B2 | 10/2013 | Cook et al. |
| 8,562,648 B2 | 10/2013 | Kaes et al. |
| 8,580,865 B2 | 11/2013 | Peters et al. |
| 8,597,675 B2 | 12/2013 | Murphy et al. |
| 8,613,938 B2 | 12/2013 | Akella et al. |
| 8,623,094 B2 | 1/2014 | Evans et al. |
| 8,641,774 B2 | 2/2014 | Rahaman et al. |
| 8,642,061 B2 | 2/2014 | Shimp et al. |
| 8,652,503 B2 | 2/2014 | Wironen et al. |
| 8,663,326 B2 | 3/2014 | Osman |
| 8,663,672 B2 | 3/2014 | Manrique et al. |
| 8,663,677 B2 | 3/2014 | Fu et al. |
| 8,685,429 B2 | 4/2014 | Koblish et al. |
| 8,734,525 B2 | 5/2014 | Behnam et al. |
| 8,740,987 B2 | 6/2014 | Geremakis et al. |
| 8,747,899 B2 | 6/2014 | Chaput et al. |
| 8,753,391 B2 | 6/2014 | Lu et al. |
| 8,753,689 B2 | 6/2014 | Morris et al. |
| 8,758,792 B2 | 6/2014 | Behnam et al. |
| 8,778,378 B2 | 7/2014 | Clineff et al. |
| 8,795,382 B2 | 8/2014 | Lin et al. |
| 8,802,626 B2 | 8/2014 | Rueger et al. |
| 8,834,928 B1 | 9/2014 | Truncale et al. |
| 8,864,843 B2 | 10/2014 | Lu et al. |
| 8,871,235 B2 | 10/2014 | Borden |
| 8,876,532 B2 | 11/2014 | Atkinson et al. |
| 8,877,221 B2 | 11/2014 | McKay |
| 8,883,210 B1 | 11/2014 | Truncale et al. |
| 8,926,710 B2 | 1/2015 | McKay |
| 8,992,964 B2 | 3/2015 | Shelby et al. |
| 8,992,965 B2 | 3/2015 | Behnam |
| 9,029,077 B2 | 5/2015 | Song et al. |
| 9,066,994 B2 | 6/2015 | Scarborough |
| 9,162,012 B2 | 10/2015 | Benham et al. |
| 9,486,500 B2 | 11/2016 | McKay |
| 9,486,557 B2 | 11/2016 | Carter et al. |
| 9,572,912 B2 | 2/2017 | Scarborough et al. |
| 9,623,153 B2 | 4/2017 | McKay |
| 9,642,936 B2 | 5/2017 | Scarborough |
| 9,675,645 B2 | 6/2017 | Wei |
| 9,717,822 B2 | 8/2017 | Behman et al. |
| 9,788,950 B1 | 10/2017 | Weston et al. |
| 10,130,736 B1 | 11/2018 | Semler et al. |
| 10,173,375 B2 | 1/2019 | Meyer et al. |
| 10,300,170 B2 | 5/2019 | Masinaei et al. |
| 10,357,511 B2 | 7/2019 | Behnam et al. |
| 10,531,957 B2 | 1/2020 | McCallister et al. |
| 11,007,305 B1* | 5/2021 | Carter .................... A61L 27/34 |
| 2001/0038848 A1 | 11/2001 | Donda et al. |
| 2002/0076429 A1 | 6/2002 | Wironen et al. |
| 2002/0098222 A1 | 7/2002 | Wironen et al. |
| 2002/0193883 A1 | 12/2002 | Wironen |
| 2002/0197242 A1 | 12/2002 | Gertzman |
| 2003/0009235 A1 | 1/2003 | Manrique et al. |
| 2003/0055512 A1 | 3/2003 | Genin et al. |
| 2003/0149437 A1 | 8/2003 | Livne et al. |
| 2004/0091462 A1 | 5/2004 | Lin et al. |
| 2005/0118230 A1 | 6/2005 | Hill et al. |
| 2005/0251267 A1 | 11/2005 | Winterbottom et al. |
| 2005/0281856 A1 | 12/2005 | McGlohorn et al. |
| 2006/0018942 A1 | 1/2006 | Rowe et al. |
| 2006/0036331 A1 | 2/2006 | Lu et al. |

(56) References Cited

U.S. PATENT DOCUMENTS

| | | |
|---|---|---|
| 2006/0147545 A1 | 7/2006 | Scarborough et al. |
| 2007/0083270 A1 | 4/2007 | Masinaei et al. |
| 2007/0098756 A1 | 5/2007 | Behnam |
| 2007/0105222 A1 | 5/2007 | Wolfinbarger et al. |
| 2007/0110820 A1 | 5/2007 | Behnam |
| 2007/0113951 A1 | 5/2007 | Huang |
| 2008/0033572 A1 | 2/2008 | D'Antonio et al. |
| 2008/0069852 A1 | 3/2008 | Shimp et al. |
| 2008/0091270 A1 | 4/2008 | Miller et al. |
| 2008/0152687 A1 | 6/2008 | Thorne |
| 2008/0187571 A1 | 8/2008 | Clineff et al. |
| 2008/0262633 A1 | 10/2008 | Williams |
| 2009/0012625 A1 | 1/2009 | Ying et al. |
| 2009/0074753 A1 | 3/2009 | Lynch |
| 2009/0157087 A1 | 6/2009 | Wei et al. |
| 2009/0192474 A1 | 7/2009 | Wei et al. |
| 2009/0312842 A1 | 12/2009 | Bursac et al. |
| 2009/0317447 A1 | 12/2009 | Hsiao et al. |
| 2010/0055078 A1 | 3/2010 | Hughes-Fulford |
| 2010/0098673 A1 | 4/2010 | D'Antonio |
| 2010/0145469 A1 | 6/2010 | Barralet et al. |
| 2010/0196333 A1 | 8/2010 | Gaskins et al. |
| 2010/0203155 A1 | 8/2010 | Wei et al. |
| 2010/0234966 A1 | 9/2010 | Lo |
| 2011/0045044 A1 | 2/2011 | Masinaei et al. |
| 2011/0066242 A1 | 3/2011 | Lu et al. |
| 2011/0070312 A1 | 3/2011 | Wei et al. |
| 2011/0117018 A1 | 5/2011 | Hart et al. |
| 2011/0117165 A1 | 5/2011 | Melican et al. |
| 2011/0117166 A1 | 5/2011 | Melican |
| 2011/0117171 A1 | 5/2011 | Melican et al. |
| 2011/0144764 A1 | 6/2011 | Bagga et al. |
| 2011/0224675 A1 | 9/2011 | Tofighi et al. |
| 2011/0262554 A1 | 10/2011 | Masinaei et al. |
| 2011/0276147 A1 | 11/2011 | Cook et al. |
| 2011/0280924 A1 | 11/2011 | Lin et al. |
| 2012/0053692 A1 | 3/2012 | Voor et al. |
| 2012/0064290 A1 | 3/2012 | Esat et al. |
| 2012/0093895 A1 | 4/2012 | Song et al. |
| 2012/0164187 A1 | 6/2012 | Ollila et al. |
| 2012/0195971 A1 | 8/2012 | Missos et al. |
| 2012/0207839 A1 | 8/2012 | Liu |
| 2012/0237568 A1 | 9/2012 | Murphy et al. |
| 2013/0013071 A1 | 1/2013 | Betz et al. |
| 2013/0059382 A1 | 3/2013 | Tsai et al. |
| 2013/0122057 A1 | 5/2013 | Garigapati et al. |
| 2013/0144376 A1 | 6/2013 | Dave et al. |
| 2013/0145963 A1 | 6/2013 | Cai et al. |
| 2013/0150227 A1 | 6/2013 | Wang et al. |
| 2013/0189338 A1 | 7/2013 | Drapeau et al. |
| 2013/0195805 A1 | 8/2013 | Wei et al. |
| 2013/0202670 A1 | 8/2013 | Darmac et al. |
| 2013/0236513 A1 | 9/2013 | Guelcher et al. |
| 2013/0244942 A1 | 9/2013 | Benedict et al. |
| 2013/0274890 A1 | 10/2013 | McKay |
| 2013/0282138 A1 | 10/2013 | McKay |
| 2013/0297038 A1 | 11/2013 | McKay |
| 2014/0010890 A1 | 1/2014 | Borden |
| 2014/0031950 A1 | 1/2014 | Cook et al. |
| 2014/0079753 A1 | 3/2014 | Darby et al. |
| 2014/0170202 A1 | 6/2014 | Peters et al. |
| 2014/0195005 A1 | 7/2014 | McKay |
| 2014/0205674 A1 | 7/2014 | Wei |
| 2014/0212471 A1 | 7/2014 | Drapeau et al. |
| 2014/0220142 A1 | 8/2014 | Song et al. |
| 2014/0222159 A1 | 8/2014 | Bursac et al. |
| 2014/0271779 A1 | 9/2014 | Bagga et al. |
| 2014/0271786 A1 | 9/2014 | Bagga et al. |
| 2014/0271914 A1 | 9/2014 | Wagner |
| 2014/0294913 A1 | 10/2014 | Hasirci et al. |
| 2014/0314822 A1* | 10/2014 | Carter ................ A61L 27/3847 264/28 |
| 2015/0010607 A1 | 1/2015 | Francis et al. |
| 2016/0361171 A1 | 12/2016 | Wang et al. |
| 2017/0035937 A1 | 2/2017 | Southard et al. |
| 2017/0312079 A1 | 11/2017 | Schlachter et al. |
| 2018/0028317 A1 | 2/2018 | Schlacter |
| 2019/0183651 A1 | 6/2019 | Schlacter et al. |
| 2019/0255216 A1 | 8/2019 | Kalpaksi et al. |
| 2019/0314549 A1* | 10/2019 | Chen ................ A61K 38/1875 |
| 2019/0314550 A1 | 10/2019 | Brahm |
| 2022/0008615 A1* | 1/2022 | Cige ........................ A61F 2/28 |

FOREIGN PATENT DOCUMENTS

| | | |
|---|---|---|
| EP | 1638486 A | 12/2004 |
| JP | 2003503159 A | 1/2003 |
| JP | 2004501719 A | 1/2004 |
| WO | 2004110308 A2 | 12/2004 |
| WO | 2005084701 A1 | 9/2005 |
| WO | 2014128289 A1 | 8/2014 |
| WO | 2016077718 A1 | 5/2016 |
| WO | 2019033082 A1 | 2/2019 |

* cited by examiner

BIOMATERIAL IMPLANTS AND METHODS OF MAKING THE SAME

FIELD OF THE INVENTION

The present application relates generally to bone and wound healing biomaterials and implants formed therefrom, methods of making the biomaterials and implants, methods of promoting bone or wound healing in a mammal, and kits that include one or more of the biomaterials, implants, or components thereof.

BACKGROUND OF THE INVENTION

Bone grafting is a surgical procedure that replaces missing bone and/or repairs bone. Bone generally has the ability to regenerate but may require a scaffold to do so. Bone grafts may be allograft (cadaveric bone e.g., from a bone bank), autologous (i.e., bone harvested from the patient's own body, for example from the iliac crest), or synthetic. The bone grafts may be resorbed and replaced as the natural bone heals over time.

Biomaterials may include osteoconduction (guiding the reparative growth of the natural bone), osteoinduction (encouraging undifferentiated cells to become active osteoblasts), osteostimulative (active stimulation of osteoblast proliferation and differentiation) and/or osteogenesis (living bone cells in the graft material contributing to bone remodeling). Although traditional bone grafts may exhibit certain advantages, traditional allograft may not exhibit the properties desired, may be difficult to obtain, or may not be in a shape or form suitable for implantation.

SUMMARY OF THE INVENTION

To meet this and other needs, biomaterials described herein may be advantageous for bone healing and repair and without the drawbacks of present allograft or autograft products. The biomaterial compositions or implants prepared therefrom may include demineralized bone matrix (e.g., in the form fibers) alone or combined with additional components. If desired, the biomaterial composition may also include a carrier such as poloxamer, glycerol, carboxymethyl cellulose, or sodium hyaluronate.

According to one embodiment, a bone graft or implantable biomaterial for aiding bone regeneration includes only entangled and compressed demineralized cortical fibers. The bone graft may be produced by obtaining whole bone, debriding and sectioning the whole bone shafts into cortical rings, machining the cortical rings into cortical fibers having lengths of 10-50 mm, widths of 0.5-2 mm, and thicknesses of 0.1-1 mm, demineralizing the cortical fibers, suspending and entangling the demineralized cortical fibers in an aqueous solution, compressing the demineralized cortical fibers in a mold for a time and with pressure sufficient to form a molded biomaterial composition of a given shape, freezing the molded biomaterial composition, and freeze-drying the molded biomaterial composition to form the implantable biomaterial. Any excess water present following suspension of demineralized cortical fibers may be drained from the bone graft before, during and/or after the molding process.

The cortical rings may be sectioned into lengths of 10-30 mm. The cortical rings may be cleaned with a 0.1% v/v sodium deoxycholate/sterile saline solution, a 3% hydrogen peroxide solution, a 70% isopropyl alcohol solution, and warm sterile water. Two-thirds of the cortical ring wall thickness may be machined into fibers and the remaining one-third may be discarded. The fibers may be demineralized using an acid treatment with a 0.6N-1N hydrochloric acid treatment followed by a buffer rinse to obtain a neutral pH. The demineralized cortical fibers may be suspended in sterile water and entangled under agitation. The cortical fibers may be compressed in the mold and drain holes in the mold may allow for drainage of excess water. The mold may be packed at a 1:1 to 2:1 ratio, in cubic centimeters, of demineralized cortical fiber to mold volume. The loaded mold may be frozen and subsequently freeze-dried to produce the final product. Prior to use, the dried implantable biomaterial may be reconstituted with saline or a cellular material, such as red blood cells, white blood cells, platelets, blood plasma, and/or bone marrow cells.

According to another embodiment, a bone graft or implantable biomaterial for aiding bone regeneration includes only a mixture of about 66% demineralized cortical fibers having lengths of 15-30 mm and about 33% non-demineralized cortico-cancellous chips having a size less than 1 mm (e.g., a ratio of 2:1 fibers to chips). The bone graft may be produced by obtaining whole bone, debridement of soft tissues, sectioning the whole bone into condyles and cortical shafts, grinding the condyles into cortico-cancellous chips having a size less than 1 mm, sectioning cortical shafts into cortical rings and machining the cortical rings into cortical fibers, demineralizing the cortical fibers, combining the cortico-cancellous chips and demineralized cortical fibers in a mixture including about 66% demineralized cortical fibers and about 33% non-demineralized cortico-cancellous chips, molding the demineralized fibers in a mold to form a molded biomaterial composition of a given shape, optionally freezing the filled mold, and freeze-drying the molded biomaterial composition to form the implantable biomaterial.

According to another embodiment, the bone graft may be in the form of a gel, putty, crunch, or strip. The gel may include a combination of cortico-cancellous chips and reverse phase hydrogel carrier. The gel may include 30-60% demineralized cortico-cancellous chips and 40-70% carrier. The putty and crunch may include a combination of cortico-cancellous chips, demineralized cortical fibers, and reverse phase hydrogel carrier. The putty may include 40-70% demineralized cortical fibers, 20-40% cancellous chips in a size range of 100-500 μm, and 10-40% carrier solution. The crunch may include 40-70% cortical fibers, 10-30% cancellous chips in a size range of 100-500 μm, 10-30% cancellous chips in a size range of 500-1500 μm, and 10-40% carrier solution. The strip may include cortico-cancellous chips and demineralized cortical fibers. The strip may include 75% demineralized cortical fibers and 25% cortico-cancellous chips having a size in a range of 100-500 μm. The strip may be freeze-dried and crosslinked. For example, the strips may be cross-linked with a 0.25% glutaraldehyde or formaldehyde solution for about one minute.

The condyles and cortical shafts may undergo a liquid processing including an antibiotic/antimycotic solution for 10-15 minutes, 0.05-0.15% v/v sodium deoxycholate solution for 15-35 minutes, 2-6% (w/v) hydrogen peroxide solution for 15-35 minutes, and 70% isopropyl alcohol for 5-15 minutes with intermediate rinse steps using sterile water. The cortico-cancellous chips may have a unimodal or bimodal distribution (e.g., 100-500 μm and 500-1500 μm). The carrier may be a 25-45% (w/v) solution with poloxamer, glycerol, carboxymethyl cellulose, or sodium hyaluronate. For example, the carrier may be a 35% (w/v) solution with poloxamer.

According to yet another embodiment, a method of promoting bone or wound healing in a mammal includes providing a compressed, freeze dried implantable biomaterial comprised of demineralized bone in fiber form; and administering the implantable biomaterial into a target repair site to facilitate repair or regeneration of bone at the target repair site. The target repair site may include an injury or defect in the spine. The implantable biomaterial may form a standalone implant configured to be positioned between adjacent vertebrae or may be positioned in or near a cage or other suitable interbody device.

According to yet another embodiment, a kit includes one or more biomaterials, implants, or components thereof described herein. For example, the kit may contain putty, gel, strip, crunch, and/or boat versions of the biomaterial compositions. The kit may contain biomaterial compositions of the same or different types. In addition, the kit may include other components known in the art, including, but not limited to, carriers or scaffolds, cages or interbody devices (e.g., titanium and/or polyether ether ketone (PEEK) spacers), allograft spacers, cell culture media, phosphate buffered saline (PBS), a tissue culture substrate, bone graft harvesting tools, bone marrow aspirate retrieval tools, or the like.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

The present application relates generally to biomaterials and implants made therefrom, methods of making the biomaterial and implants, methods of promoting bone or wound healing in a mammal by administering the biomaterial or implant to the mammal, and kits that include one or more of the biomaterials, implants, or components thereof are also provided.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments of modifications thereof are contemplated as falling within the scope of this disclosure and equivalents thereto.

In describing example embodiments, specific terminology is employed for the sake of clarity. However, the embodiments are not intended to be limited to this specific terminology. Unless otherwise noted, technical terms are used according to conventional usage.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of."

Unless specified otherwise, all values provided herein include up to and including the endpoints given, and the values of the constituents or components of the compositions are expressed in weight percent or % by weight of each ingredient in the composition.

Each compound used herein may be discussed interchangeably with respect to its chemical formula, chemical name, abbreviation, etc. For example, PEG may be used interchangeably with polyethylene glycol.

Embodiments described herein may be generally directed to biomaterials, implants made therefrom, methods of making the same, and methods of using the same to promote healing or fusion of bone. Although biomaterials or implants may be discussed separately, it will be appreciated by one of ordinary skill in the art that the biomaterials described may be used in and of itself or may be used to create implants of different shapes, sizes, and orientations for a number of different clinical outcomes. Thus, the discussion of biomaterials may apply equally to the discussion on implants and vice versa.

The biomaterial composition may be osteoconductive, osteoinductive, osteogenic, and/or osteostimulative, which may be advantageous for bone healing and repair. The biomaterials may be osteoconductive when the material serves as a scaffold that provides surface area for new bone growth. The biomaterials may be osteoinductive if they stimulate osteoprogenitor cells or induce mesenchymal stem cells to differentiate into osteoblasts that then begin new bone formation. Biomaterials may be osteogenic if they contain cells (e.g., viable cells) that are capable of bone regeneration. The biomaterial may be osteostimulative if the material accelerates the bone formation process.

The composition may be "biocompatible" as that term refers to the ability (e.g., of a composition or material) to perform with an appropriate host response in a specific application, or at least to perform without having a toxic or otherwise deleterious effect on a biological system of the host, locally or systemically. The biomaterial and/or implant may be "biologically degradable" in that the material may be degraded by cellular absorption and/or hydrolytic degradation in a patient's body. According to some embodiments, it may be desirable that the biomaterials possess sufficient osteoconductivity, porosity, mechanical strength, and degradation times.

According to one embodiment, the biomaterial composition may be configured to facilitate repair or regeneration of bone at a target repair site. The target repair site can be, for example, a void, gap, or other defect or surgeon created opening in a bone, between bones, or other bony structure in a body of a patient. For example, the biomaterial composition can be configured to facilitate bone growth at a target repair site in the spine, pelvis, an extremity, the cranium, or another bone, between bones, or bony structure in the patient's body. The biomaterial composition may be configured to be directly implanted or otherwise disposed at or in contact with the target repair site.

The biomaterial composition may include demineralized bone matrix (e.g., in the form of fibers, chips, or particulates), and optionally one or more additional components each of which is described in more detail herein. Demineralized bone matrix (also known as DBM) may provide osteoconductive, osteoinductive and/or osteogenic properties. Thus, it induces the formation of bone tissue. As used herein, the terms "demineralized bone", "demineralized bone matrix", and "DBM" may be used interchangeably. The demineralized bone, for example, in the form of fibers, chips, and/or particles, can be disposed on, embedded within, and/or mixed within the biomaterial composition.

Demineralized bone matrix may be in the form of fibers, threads, strips, chips, shards, sheets, elongated particles, powder, or particulates, for example. The demineralized bone matrix may include bone pieces of varying shapes, sizes, thickness, and configurations that possess regular, irregular, or random geometries. In some embodiments, the bone used to manufacture the demineralized bone matrix may be cortical, cancellous, cortico-cancellous of autogenous, allogeneic, xenogeneic or transgenic in origin. Thus, the fibers, chips, or particulates, for example, may include cortical, cancellous, or cortico-cancellous bone unless specified otherwise.

To prepare bone matrix, the bone material may be treated to clean, defat, sterilize, virally inactivate, disinfect, demineralize, dehydrate, and/or dry the bone matrix. Methods for preparing demineralized bone matrix may include, but are not limited to, shaving bone into thin shavings or fibers, milling, grinding, or crushing bone into chips or particles, or the like. Before or after processing the bone, the bone material may be subjected to demineralization so as to reduce inorganic content to low levels. For example, demineralized bone may be produced by acid extraction, thermal freezing, irradiation, or physical extraction of inorganic minerals from human or animal bone. In an acid extraction, inorganic acids such as hydrochloric acid or phosphoric acid, or organic acids such as formic acid, acetic acid, peracetic acid, citric acid, propionic acid, etc. may be used. As would be recognized by one of ordinary skill in the art, the amount and depth of demineralization into the bone surface can be controlled by adjusting the treatment time, temperature of the demineralizing solution, concentration of the demineralizing solution, agitation intensity during treatment, and the like.

The term "demineralized" refers to bone or bone material containing less than its original mineral content (e.g., calcium content) and may encompass "substantially demineralized," "partially demineralized," and "completely demineralized" bone material. For example, the demineralized bone may include less than 10%, less than 9%, less than 8%, less than 7%, less than 6%, less than 5%, less than 4%, less than 3%, less than 2%, or less than 1% of the original mineral content (e.g., calcium content) of the bone.

According to one embodiment, the demineralized bone matrix includes only demineralized cortical bone fibers that are suspended, entangled and compressed to form demineralized cortical fiber strips. The process produces an allograft with ideal handling characteristics for use in surgical applications, for example, as bone void filler, without the need for chemical crosslinking or an added carrier. The demineralized cortical bone fiber allograft may be in the form of a molded strip, which maintains structural integrity, pliability, compressibility, osteoconductivity, and osteoinductive potential. The demineralized cortical fiber strips also provide a high surface area scaffold for potential cellular adhesion and migration due to the physical dimensions of the cortical fibers within the molded allograft.

Figure 1:
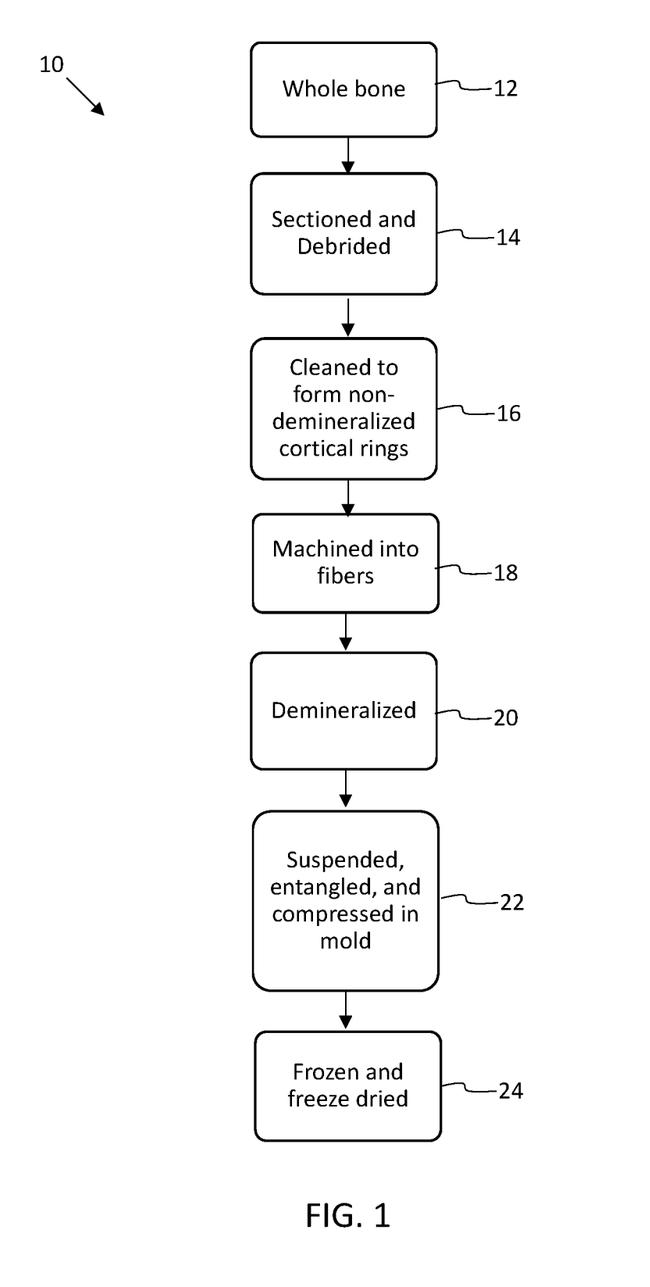
FIG. 1 shows a process flowchart of the steps for producing a demineralized cortical fiber allograft according to one embodiment.

Referring now to FIG. 1, a process 10 for preparing the demineralized cortical fiber strips may include one or more of the following steps. Whole bone is obtained in step 12. The whole bones may include long bones, such as femur, tibia, humerus, radius and ulna, or other suitable bones. The bones may be obtained from human or other animal sources. The whole bones may be sectioned and debrided in step 14. The whole bones may be sectioned into cortical rings, for example, in lengths of about 10-50 mm, about 20-40 mm, about 20-30 mm, or about 28-30 mm. Each cortical ring central canal is then debrided or cleared in preparation for liquid processing. The cortical rings may be cleaned in step 16, prior to fiber generation. For example, the cortical rings may be cleaned with chemical and/or physical cleaning procedures that reduce the bone marrow and lipid elements associated with normal human tissue. The cleaning procedure may use one or more liquid solutions for suitable time periods to ensure thorough cleaning. For example, the cortical rings may be cleaned with a 0.1% v/v sodium deoxycholate/sterile saline solution, a 3% hydrogen peroxide solution, a 70% isopropyl alcohol solution, warm sterile water, combinations of these, or other suitable solutions.

In step 18, the non-demineralized cortical rings are machined into cortical fibers. The cortical fibers may be produced, for example, with a horizontal milling machine. In one embodiment, the cortical fibers are produced with an end mill having about a 0-30 degree helix angle. The cortical rings may be loaded onto the machine vise and fed across the cutting surface to produce the cortical fibers. In one embodiment, about two-thirds of the cortical ring wall thickness is milled, and the remaining one-third is discarded. It will be appreciated that the entire cortical wall thickness may be milled or any suitable portion thereof. In step 18, the non-demineralized cortical rings may be machined into thin fibers, for example, of lengths of about 10-50 mm, widths of about 0.5-2 mm, and thicknesses of about 0.1-1 mm. It will be appreciated that some variation in dimension is possible in the production of the fibers.

The non-demineralized cortical fibers then undergo a demineralization process in step 20 to remove the mineral components of bone. For example, the demineralization may include an acid treatment with a 0.6N-1N hydrochloric acid treatment. The acid treatment may be followed by a buffer rinse to obtain a neutral pH (e.g., 6.8-7.4). Once demineralized, the demineralized cortical fibers are suspended, entangled, and compressed in a mold in step 22. The demineralized cortical fibers may be suspended in an aqueous solution. The aqueous solution may include water and an optional solute. For example, the fibers may be suspended in sterile water, deionized water, distilled water, or purified water. While in solution, the demineralized cortical fibers may be entangled naturally or by agitation. The entangled solution of fibers is compressed in a mold. The mold may contain drain holes for the removal of excess water. Each mold cavity may be packed at a 1:1 to 2:1 ratio of cortical fiber to mold volume (cc's). In step 24, the packed molds are then frozen and placed into a freeze dryer to produce the final freeze-dried strip product.

The dried allograft may be reconstituted at time of use, for example, in less than 5 minutes. For example, the allograft may be reconstituted with an acceptable sterile irrigant (e.g., saline). The dried allograft may also be reconstituted with a cellular material such as chondrocytes, red blood cells, white blood cells, platelets, blood plasma, bone marrow cells, mesenchymal stem cells, pluripotential cells, osteoblasts, osteoclasts, and fibroblasts, epithelial cells, and endothelial cells.

The properties of the demineralized cortical fiber allograft maintain structural integrity, pliability, and compressibility at lower cortical fiber densities than other compositions. The process produces consistent densities and mechanical properties per product. The cortical fiber structure provides a larger surface area than cancellous bone and other demineralized bone matrix products with cancellous or cortical fiber chips making the cortical fiber allograft a superior osteoconductive scaffold than other allografts.

According to another embodiment, the bone graft is a mixture of osteoinductive demineralized cortical bone fibers and osteoconductive cortico-cancellous chips. Autograft, obtained from the patient, may be desirable for the generation of new bone. Due to limited availability and donor site morbidity, however, there are drawbacks to autograft. Accordingly, the development of matrices that possess osteoconductive and osteoinductive components to promote bone regeneration are desirable in the area of bone repair. The demineralized bone matrix has osteoinductive properties due to intrinsic growth factors, such as bone morphogenic proteins (BMP), in the bone. In this embodiment, a scaffold with osteoconductive and osteoinductive properties is used to aid in bone regeneration. The demineralized cortical fibers allow for increased surface area of the product, which promotes increased cell adhesion and interaction with growth factors following implantation.

Figure 2:
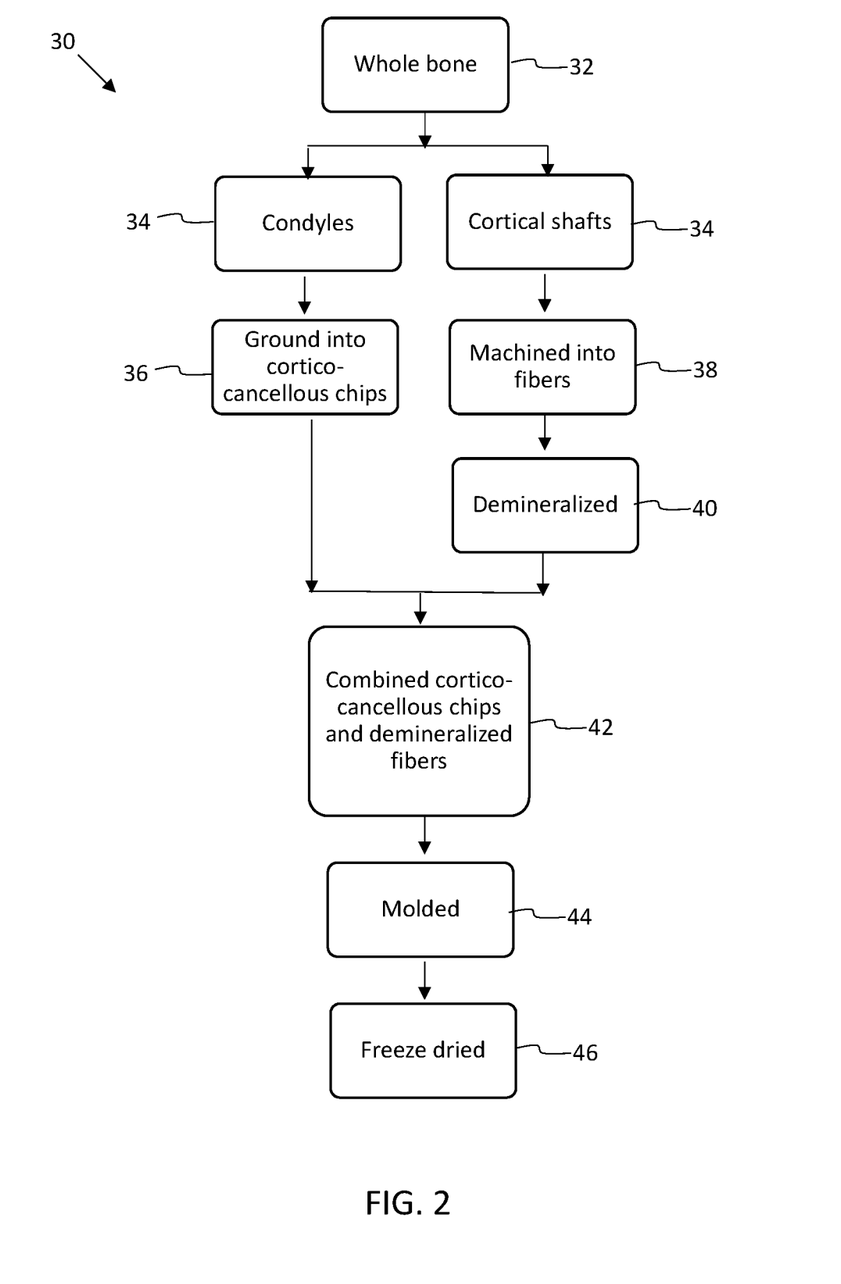
FIG. 2 shows a process flowchart of the steps for producing a demineralized cortical fiber and non-demineralized cortico-cancellous chip allograft according to one embodiment.

With reference to FIG. 2, a process 30 for preparing the demineralized cortical fiber and non-demineralized cortico-cancellous bone graft may include one or more of the following steps. Whole bone is obtained in step 32. The whole bones, such as long bones including femur, tibia, radius and ulna, or other suitable bones may be processed. The bones may be obtained from human or other animal sources. In step 34, the condyles of the long bones are separated from the cortical shafts. The cortical shafts are completely cleaned to remove any fat tissue and marrow. Cortical shafts are subsequently sectioned into cortical rings. In step 36, the condyles are cut into smaller wedges and ground, for example, using a bone mill to produce cortico-cancellous chips and/or cancellous chips. The size of the cortico-cancellous chips may be less than about 1 mm, about 100 µm-1 mm, or about 100-500 µm. The product may or may not include cortico-cancellous chips. In step 38, the cortical rings are machined into cortical fibers. The cortical fibers are then demineralized in step 40. The cortical fibers may be demineralized using an acid extraction, for example, with 0.5-1N hydrochloric acid. In step 42, the non-demineralized cortico-cancellous chips and the demineralized cortical fibers are combined. The mixture may include demineralized cortical fibers in an amount of about 50-100%, about 66-100%, about 66-80%, about 60-70% or about 66%. The mixture may include cancellous chips in an amount of about 0-50%, about 0-33%, about 20-33%, about 30-40%, or about 33%. In one embodiment, the formulation includes demineralized cortical fibers and non-demineralized cortico-cancellous chips premixed at a 2:1 ratio.

The bone graft may be in the form of a putty, strip, or boat, for example. The putty, strip, or boat formulations may each use the same base mixture. For the strip and boat, in step 44, the mixture is transferred to molds. The biomaterial composition may be added to the mold to form a molded biomaterial composition. The form or mold may be of any suitable size and shape to obtain the desired shaped implant or a portion thereof. The mold may be provided under a given pressure and temperature necessary to form a compressed implant. The composition may be compressed for a time and pressure sufficient to create the desired shaped implant or a portion thereof. The pressure exerted upon the biomaterial composition may cause the components to contact one another and adhere together. The mold may be provided under an elevated pressure (i.e., greater than atmospheric) sufficient to compress the biomaterial into a solid form. Alternatively, the composition may be placed in a mold with no compression. If desired, a pattern or design may be cut into or out of the molded implant to form other desired shapes. In step 46, the composition is freeze-dried. Freeze-drying may include freezing the biomaterial (e.g., in liquid nitrogen) and reducing the surrounding pressure to allow the frozen water in the material to sublimate directly from the solid phase to the gas phase. Prior to use, the dried allograft may be reconstituted, for example, with saline or a suitable cellular material.

Figure 3A:
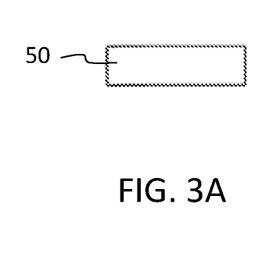
FIGS. 3A-3C depict an allograft in strip form according to one embodiment.
Figure 3B:
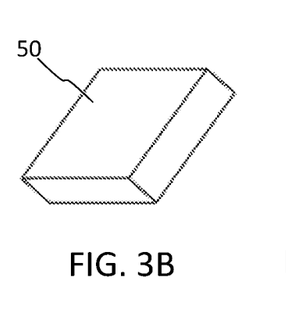
Figure 3C:
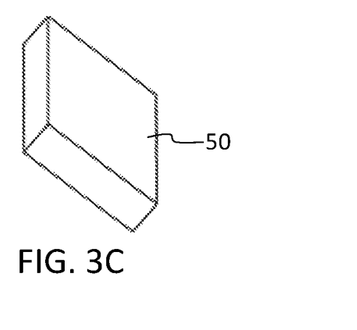
Figure 4A:
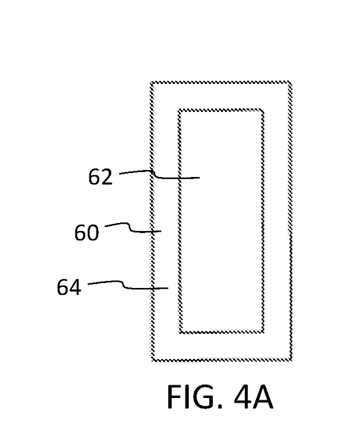
FIGS. 4A-4F depict an allograft in boat form according to one embodiment.
Figure 4B:
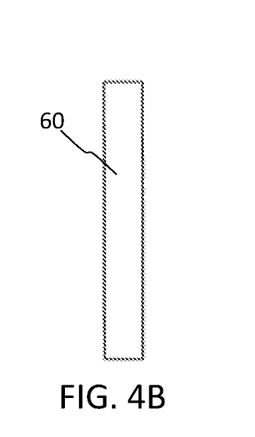
Figure 4C:
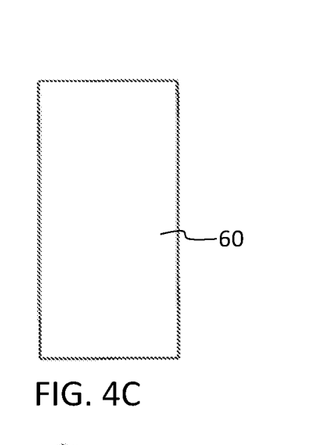
Figure 4D:
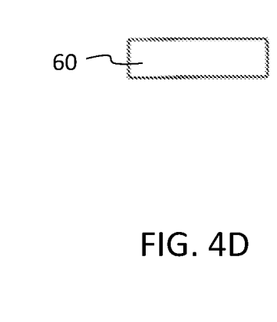
Figure 4E:
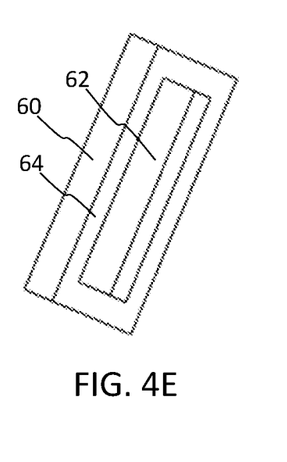
Figure 4F:
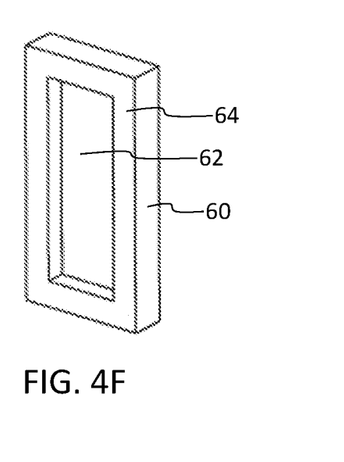

The putty, strip, and boat may have a length, thickness, and width. FIGS. 3A-3C show side and perspective views, respectively, of a strip 50. The strip 50 may be generally quadrilateral in shape (e.g., rectangular). The resulting implant may be molded to have substantially planar side walls. As shown in FIGS. 3A-3C, the top and bottom bone engaging surfaces may be substantially flat or planar. It is also envisioned that the top and bottom, bone engaging surfaces may be curved, angled, or of any suitable shape to better fit the anatomy of the adjacent vertebrae. Alternatively, the bone engaging surfaces may include protrusions, teeth, or the like. FIGS. 4A-4F show top, side, bottom, front, and perspective views, respectively, of a boat 60. The boat 60 may have an indentation 62 in the center providing a raised periphery 64 around the edges. The indentation 62 in the center of the boat 60 may allow the surgeon to pack bone material therein (e.g., autologous bone). The strips and boats may come in lengths up to about 200 mm, thicknesses of about 4-10 mm, and widths of about 10-25 mm. The large indentation 62 in the center of the boat 60 may be about 2-10 mm from each edge with a depth of about 2-5 mm. The putty may come in lengths up to about 200 mm, thicknesses of about 4-15 mm, and widths of about 5-25 mm.

The biomaterial may be formed into a specific size and shape for a desired application. For example, the implant may have a footprint suitable for cervical, thoracic, or lumbar applications. The implant may be shaped, for example, in the form of a strip, boat, ring, cylinder, plug, or the like. The implant may be provided with one or more openings or windows suitable to be filled with the biomaterials described herein or other graft materials known in the art. The implant may be used alone or in combination with a cage, frame, allograft, autograft, graft material, or other biomaterials known in the art. The implants may be suitable for an anterior, posterior, lateral, oblique, anterolateral, transforaminal approach, or other suitable approach known in the art.

The use of demineralized cortical fibers may provide a higher surface area for interactions with cells and the local environment. The demineralizing process exposes native growth factors in the fibers, which may help to promote bone repair. The cancellous chips provide additional scaffolding for cells to adhere to as well as additional bulking material for the product. The chips may help to resist compression of the product, mitigating the perception that volume utilized is less than it should be due to the compressive nature of the fibers. Working together, the components provide cohesive, putty-like handling characteristics for the putty form. For the strip and boat, the freeze-dried and entangled components allow for a product that maintains structural integrity when utilized, while also being flexible enough to match the contours of the bony anatomy at the application site.

According to another embodiment, the bone graft is a mixture of demineralized fibers, non-demineralized and/or demineralized cortico-cancellous chips, and an optional carrier. The carrier may affect the overall handling of the material and may influence the safety, efficacy, and functionality of the material (e.g., osteoinductivity). Preferably, the carrier is inert or enhances osteogenic, osteoinductive, osteoconductive, and/or osteostimulative properties of the composition. Suitable carriers, scaffolds, or additives may include, but are not limited to, poloxamers, hydrogels, phospholipids, carboxylmethylcellulose (CMC), glycerin, glycerol, polyethylene glycol (PEG), polylactic acid (PLA), polylactic-co-glycolic acid (PLGA), other copolymers of the same family, and combinations thereof.

By way of example, the carrier may include a hydrogel, including a reverse phase hydrogel or temperature sensitive hydrogel, such as a poloxamer (e.g., a PEO-PPO-PEO triblock copolymer). In particular, the poloxamer may include poloxamer 407, poloxamer P188, poloxamer P338, or the like. The poloxamer may also be chemically modified, for example, where one or more of the terminal hydroxyl groups are replaced with methoxy groups. Other suitable materials may include hyaluronic acid (HA), sodium alginate, saline or bone marrow aspirate, for instance. The carrier, scaffold materials, or processing additives may be either water-based or non-water based.

In the case of a hydrogel, such as a poloxamer, hyaluronic acid, or alginate, the materials may be swellable in volume. For example, the carrier (e.g., poloxamer) may be mixed with water, a buffer, or an acid, such as hydrochloric acid, nitric acid, sulfuric acid, or the like, which causes the carrier to swell in volume. As will be recognized by one of ordinary skill in the art, swelling of the hydrogel may be influenced by a number of factors, such as temperature, surface area, molecular weight, degree of crosslinking, pH, or the like.

Figure 5:
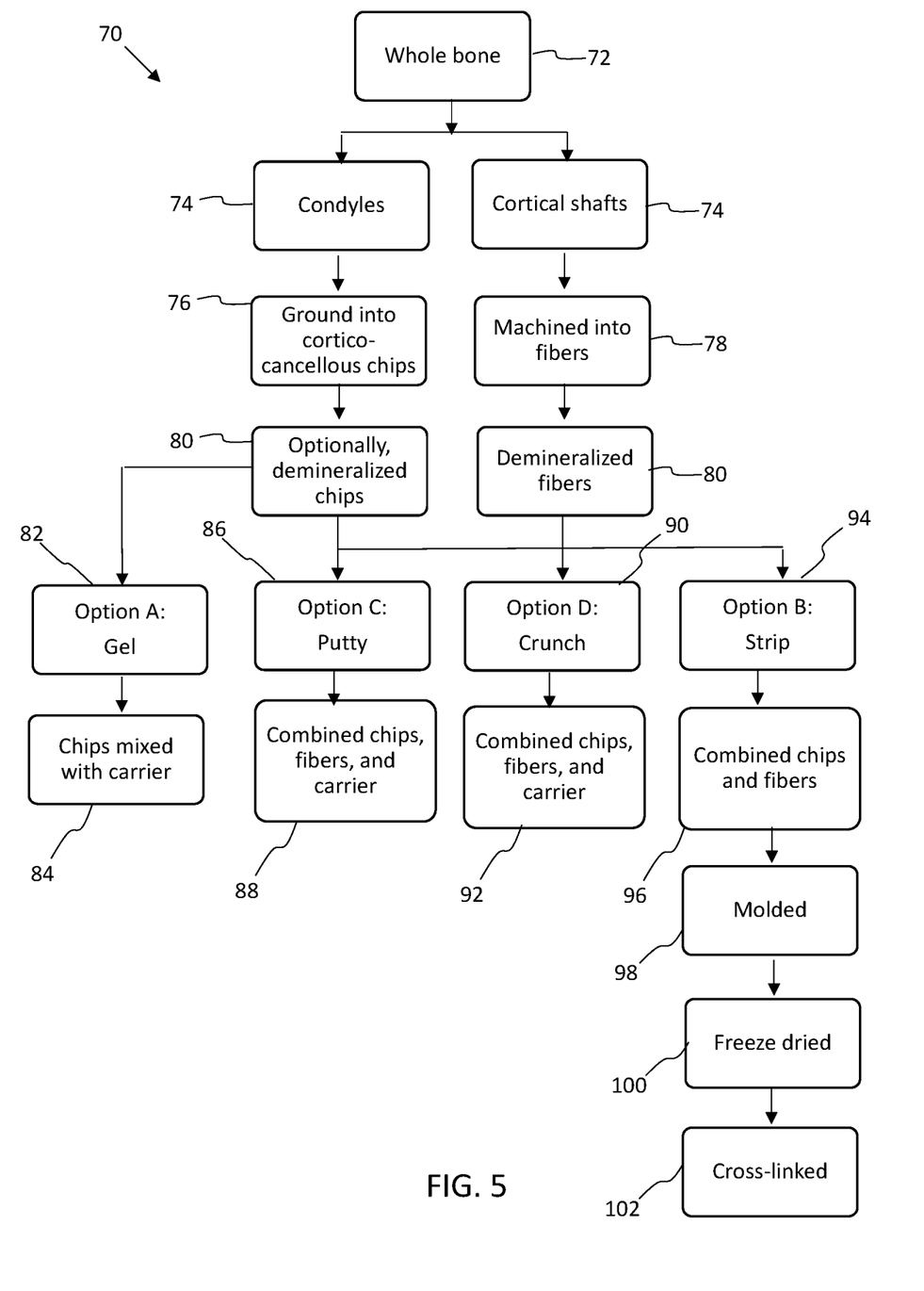
FIG. 5 shows a process flowchart of the steps for producing allografts in gel, putty, crunch, or strip form according to one embodiment.

With reference to FIG. 5, a process 70 for preparing the bone graft in the form of a gel, putty, crunch, or strip may include one or more of the following steps. Whole bone is obtained in step 72. The whole bones, such as long bones including femur, tibia, humerus, radius and ulna, or other suitable bones may be processed. The bones may be obtained from human or animal sources. In step 74, the condyles of the long bones are separated from the cortical shafts. The cortical shafts are completely cleaned to remove any fat tissue and marrow and subsequently sectioned into cortical rings. The condyles and/or the cortical rings may undergo a liquid processing. The liquid processing may include one or more of an antibiotic/antimycotic solution for 10-15 minutes, 0.05-0.15% v/v sodium deoxycholate solution for 15-35 minutes, 2-6% (w/v) hydrogen peroxide solution for 15-35 minutes, 70% isopropyl alcohol for 5-15 minutes, intermediate rinse steps using sterile water, combinations of these, or other suitable solutions. In step 76, the condyles are cut into smaller wedges and ground, for example, using a bone mill to produce cortico-cancellous chips and/or cancellous chips. The size of the cortico-cancellous chips may be less than about 1.5 mm, about 100 µm-1.5 mm, about 500-1.5 mm, about 100 µm-1 mm, or about 100-500 µm. The cortico-cancellous chips may have a unimodal or bimodal distribution. For example, the cortico-cancellous chips may be divided into two size distributions: a first size of 100-500 µm and a second size of 500-1500 µm. The product may or may not include cortico-cancellous chips.

In step 78, the cortical rings are machined into cortical fibers. The cortical rings may be put through a fiber generator to produce fibers, for example, about 10-50 mm, about 20-40 mm, or about 15-30 mm in length. The fibers and optionally the chips are then demineralized in step 80. The fibers and/or chips may be demineralized using an acid extraction, for example, with 0.5-1N hydrochloric acid for about 15-40 minutes. At the end of the treatment, the hydrochloric acid may be decanted and the fibers/chips may be rinsed in 25/75 mono-dibasic potassium phosphate solution and/or deionized water until the pH is between 6.5 and 7.5.

In option 82, the allograft may be produced as a gel form. The gel may include demineralized cortical-cancellous bone chips mixed with a carrier in step 84. The carrier may include a reverse phase hydrogel carrier solution. The bone chips may be about 100-500 µm in size. The carrier may be prepared as a 35% (w/v) solution with a thickening material, such as poloxamer 407, glycerol, carboxymethyl cellulose, or sodium hyaluronate. The carrier material may compose about 40-70% of the final product. The gel product is in an extrudable form.

In option 86, a putty may be formed. The putty may include demineralized cortical fibers, non-demineralized cortico-cancellous chips, and optionally demineralized cortico-cancellous chips mixed with a carrier in step 88. The carrier may include a reverse phase hydrogel carrier. The carrier may be prepared as a 25-45% (w/v) solution with a thickening material, such as poloxamer 407, glycerol, carboxymethyl cellulose, or sodium hyaluronate. The putty may include about 40-70% demineralized cortical fibers, about 20-40% cancellous chips (e.g., 100-500 µm), and about 10-40% carrier solution.

In option 90, the allograft may be produced in a crunch form. The crunch may include demineralized cortical fibers, non-demineralized cortico-cancellous chips, and optionally demineralized cortico-cancellous chips mixed with a carrier in step 92. The carrier may include a reverse phase hydrogel carrier. The carrier may be prepared as a 25-45% (w/v) solution with a thickening material, such as poloxamer 407, glycerol, carboxymethyl cellulose, or sodium hyaluronate. For the crunch formulation, the product may include about 40-70% cortical fibers, about 10-30% cancellous chips (e.g., 100-500 µm), about 10-30% cancellous chips (e.g., 500-1500 µm) and about 10-40% carrier solution. Thus, the crunch composition may include a bimodal distribution of the cortico-cancellous chips.

In option 94, a strip may be formed. The strip may include demineralized cortical fibers and cortico-cancellous chips (e.g., 100-500 µm) in step 96. For example, the fibers and chips may be premixed in a 3:1 ratio. In step 98, the mix may be transferred to molds. In step 100, the molds may be freeze dried. The composition may be dehydrated or dried, for example, by air or by freeze-drying. Freeze-drying may include freezing the material (e.g., in liquid nitrogen) and reducing the surrounding pressure to allow the frozen water in the material to sublimate directly from the solid phase to the gas phase.

In step 102, the freeze-dried strips may be partially of fully crosslinked. For example, crosslinking may occur by exposing the material to a chemical crosslinking agent including mono aldehydes such as formaldehyde, acetaldehyde, or glutaraldehyde. For example, the strips may be cross-linked with a 0.25% glutaraldehyde or formaldehyde solution for about one minute, followed by rinsing with water, and additional freeze drying. Chemical crosslinking may also include exposure to a chemical sterilizing agent, such as ethylene oxide, nitrogen dioxide, ozone, or the like. Radiation crosslinking may include exposing the material to a sterilizing source such as gamma, ultraviolet, x-ray, electron irradiation, and/or thermal sources. For example, the strips may be cross-linked through the terminal sterilization process, in which the product is subjected to about 25-35 kGy of E-beam sterilization.

The demineralized cortical fibers may provide a higher surface area for interactions with cells and the local environment. The demineralizing process exposes native growth factors in the fibers which may promote bone repair. The cancellous chips provide additional scaffolding for cells to adhere to as well as additional bulking material for the product. The chips may help to resist compression of the product, mitigating the perception that volume utilized is lessened due to the compressive nature of the fibers. The synergy of the components provides cohesive, putty-like handling characteristics for the putty and crunch forms. For the strip, the cross-linked components allow for a product that maintains structural integrity when utilized, while also being flexible enough to match the contours of the bony anatomy at the application site.

If desired, biological agents may be added to any of the biomaterials or implants described herein. These biological agents may comprise bone morphogenic protein (BMP), peptides, bone growth factors such as platelet derived growth factor (PDGF), vascular endothelial growth factor (VEGF), insulin derived growth factor (IDGF), a keratinocyte derived growth factor (KDGF), or a fibroblast derived growth factor (FDGF), stem cells, bone marrow, and platelet rich plasma (PRP), to name a few. If desired, one or more active pharmaceutical ingredients or medicaments may be incorporated into or added to the biomaterial or implant as well. Biological agents may be added in any suitable pharmaceutically acceptable and effective amounts known in the art.

The biomaterials and implants formed therefrom described herein are intended to be applied at a bone repair site, e.g., one resulting from injury or defect. The implants can be utilized in a wide variety of orthopedic, periodontal, neurosurgical, oral and maxillofacial surgical procedures. In particular, the biomaterials may be suitable for repairs of the vertebral column including spinal fusion and internal fixation; tumor surgery, e.g., deficit filling; discectomy; laminectomy; scoliosis, lordosis and kyphosis treatments. Possible clinical applications may include e.g., the treatment of spinal disc degeneration or disease, traumatic, pathologic, or stress fractures, congenital defects or fractures, or operative defects in any bone or between bones of the body.

The compositions and implants may be configured for use at various target repair sites within a body of a patient to facilitate bone growth therein. In some embodiments, the composition is configured for use at a target repair site in the patient's spine. For example, the composition can facilitate growth of bone between the body of a first vertebra and the body of a second vertebra to achieve interbody fusion of the two vertebrae. In a spinal fusion procedure, the composition may be used in conjunction with one or more mechanical supports (e.g., a cage or frame, spacer, plate, a plurality of screws and/or rods, or the like). Although the spine is described, the composition can be configured to be implanted into or at a target repair site in or at a different bone or bony structure of the patient's body.

The term "treating" and the phrases "treatment of a disease" and "treatment of a condition" refer to executing a protocol that may include the use of the compositions, devices and methods herein and/or administering one or more biomaterials to a patient (human, normal or otherwise, or other mammal), in an effort to alleviate signs or symptoms of the disease or condition. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms and does not require a cure to the ailment.

Further example embodiments are directed to kits that include components for making the present biomaterials and implants, including for example, carriers or scaffolds, cages (e.g., titanium and/or polyether ether ketone (PEEK) spacers), allograft spacers, demineralized bone materials, cell culture media, phosphate buffered saline (PBS), a tissue culture substrate such as a flask, trypsin, or mixtures, bone graft harvesting tools, bone marrow aspirate retrieval tools, or the like. Additional components, instructions and/or apparatus may also be included.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXAMPLES

Example 1

This example demonstrates how to make bone grafts that include only demineralized cortical fibers. The whole bone is sectioned and debrided to form cortical rings. The cortical rings are cleaned and machined into cortical fibers having lengths of 10-50 mm, widths of 0.5-2 mm, and thicknesses of 0.1-1 mm. Two-thirds of the cortical ring wall thickness is milled, and the remaining one-third of the cortical ring wall is discarded. The fibers are demineralized using a 0.6N hydrochloric acid treatment followed by a buffer rinse to obtain a neutral pH (6.8-7.4). Once demineralized, the cortical fibers are suspended in sterile water and entangled with one another. The entangled fibers are compressed in a mold and drain holes in the mold allow any excess water to drain. The mold is packed at a 2:1 ratio (cc) of cortical fiber to mold volume. The packed molds are frozen and freeze-dried to obtain the allograft.

Example 2

This example demonstrates how to make bone grafts that include demineralized cortical fibers and non-demineralized cortico-cancellous chips. The whole bone is separated into condyles and cortical shafts. The condyles are ground into cortico-cancellous chips of 100-500 μm. The cortical shafts are cleaned and machined into cortical fibers having lengths of 15-30 mm, widths of 0.1-2 mm, and thicknesses of 0.1-1 mm. The fibers are demineralized using a 0.5-1.0N hydrochloric acid treatment for 15-40 minutes followed by a buffer rinse to obtain a neutral pH. The demineralized cortical fibers are mixed with the non-demineralized cortico-cancellous chips in a ratio of 2:1. The mixture is transferred to molds and freeze-dried to obtain the allograft. The allograft may be in strip, boat, or putty form.

Example 3

This example demonstrates how to make bone grafts that include demineralized cortical fibers and/or cortico-cancellous chips with an optional carrier. The whole bone is separated into condyles and cortical shafts. The condyles are ground into cortico-cancellous chips with a first size of 100-500 μm and a second size of 500-1500 μm. The cortical shafts are cleaned and machined into cortical fibers having lengths of 15-30 mm, widths of 0.1-2 mm, and thicknesses of 0.1-1 mm. The fibers and optionally the chips are demineralized using a 0.5-0.7N hydrochloric acid treatment for 15-40 minutes. At the end of the treatment, the hydrochloric acid is decanted and the fibers/chips are rinsed in 25/75 mono-dibasic potassium phosphate solution and/or deionized water until the pH is 6.5-7.5. The gel, putty, crunch, and strip formulations are as follows:

|  | Gel | Putty | Crunch | Strip |
| --- | --- | --- | --- | --- |
| Demineralized cortical fibers | — | 40-70% | 40-70% | 75% |
| Non-demineralized cortico-cancellous chips (100-500 μm) | — | 20-40% | 10-30% | 25% |
| Non-demineralized cortico-cancellous chips (500-1500 μm) | — | — | 10-30% | — |
| Demineralized cortico-cancellous chips (100-500 μm) | 30-60% | — | — | — |
| Carrier | 40-70% (35% (w/v) solution with poloxamer 407, glycerol, carboxymethyl cellulose, or sodium hyaluronate) | 10-40% (25-45% (w/v) solution with poloxamer 407, glycerol, carboxymethyl cellulose, or sodium hyaluronate) | 10-40% (25-45% (w/v) solution with poloxamer 407, glycerol, carboxymethyl cellulose, or sodium hyaluronate) | — |

The strip is molded, freeze-dried, and cross-linked with 0.25% glutaraldehyde or formaldehyde for one minute followed by rinsing with water and freeze drying. The cross-linked strip provides for structural integrity while still being flexible. The gel is extrudable, and the putty and crunch have putty-like handling characteristics.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. A method of making an implantable biomaterial for aiding bone regeneration, the method comprising:
   obtaining whole bone;
   sectioning and debriding the whole bone into cortical rings;
   machining the cortical rings into cortical fibers having lengths of 10-50 mm, widths of 0.5-2 mm, and thicknesses of 0.1-1 mm;
   demineralizing the cortical fibers to form demineralized cortical fibers;
   suspending and entangling the demineralized cortical fibers in an aqueous solution;
   compressing the demineralized cortical fibers in solution in a mold to form a molded biomaterial composition of a given shape;
   freezing the molded biomaterial composition; and
   freeze-drying the molded biomaterial composition to form the implantable biomaterial;
   wherein the cortical rings are cleaned with a 0.05-0.15% v/v sodium deoxycholate solution, a 2-6% hydrogen peroxide solution, and an isopropyl alcohol solution.

2. The method of claim 1, wherein the cortical rings are sectioned into lengths of 10-30 mm.

3. The method of claim 1, wherein the cortical rings are cleaned with a 0.1% v/v sodium deoxycholate/sterile saline solution, a 3% hydrogen peroxide solution, a 70% isopropyl alcohol solution, and warm sterile water.

4. The method of claim 1, wherein an outer two-thirds of the cortical ring wall thickness is machined into fibers and a remaining one-third is discarded.

5. The method of claim 1, wherein the cortical fibers are demineralized using an acid treatment with a 0.6N hydrochloric acid treatment followed by a buffer rinse to obtain a neutral pH.

6. The method of claim 1, wherein the cortical fibers are suspended in sterile water and entangled under agitation.

7. The method of claim 1, wherein the cortical fibers are compressed in the mold and drain holes in the mold allow for drainage of excess water.

8. The method of claim 1, wherein the mold is packed at a 1:1 To 2:1 ratio, in cubic centimeters, of demineralized cortical fiber to mold volume.

9. The method of claim 1, wherein prior to use, further comprising reconstituting the dried implantable biomaterial with a cellular material.

10. The method of claim 9, wherein the cellular material is red blood cells, white blood cells, platelets, blood plasma, and/or bone marrow cells.

11. The method of claim 1, wherein the cleaning step is performed after sectioning, but prior to demineralizing.

12. A method of promoting bone or wound healing in a mammal, the method comprising:
   cleaning cortical fibers with a 0.05-0.15% v/v sodium deoxycholate solution, a 2-6% hydrogen peroxide solution, and an isopropyl alcohol solution;
   demineralizing the cleaned cortical fibers to form demineralized cortical fibers;
   entangling and compressing the demineralized cortical fibers having lengths of 10-50 mm, widths of 0.5-2 mm, and thicknesses of 0.1-1 mm into a bone graft, wherein any excess water is drained from the bone graft during compressing;
   administering the bone graft into a target repair site to facilitate repair or regeneration of bone at the target repair site.

13. The method of claim 12, wherein the target repair site is an injury or defect in the spine.

14. A method of making an implantable biomaterial for aiding bone regeneration, the method comprising:
   obtaining whole bone;
   separating the whole bone into condyles and cortical shafts;
   grinding the condyles into cortico-cancellous chips having a size less than 1.5 mm;

machining the cortical shafts into cortical fibers having a size of 15-30 mm;

demineralizing the cortical fibers;

combining the cortico-cancellous chips and demineralized cortical fibers with a carrier, wherein the carrier is a reverse phase hydrogel;

wherein prior to demineralizing, the cortical shafts are cleaned with a 0.05-0.15% v/v sodium deoxycholate solution, a 2-6% hydrogen peroxide solution, and an isopropyl alcohol solution.

15. The method of claim 14, wherein the carrier is a 25-45% (w/v) solution with poloxamer, glycerol, carboxymethyl cellulose, or sodium hyaluronate.

16. The method of claim 15, wherein the carrier is a 35% (w/v) solution with poloxamer.

17. The method of claim 14, wherein the implantable biomaterial is a putty including 40-70% demineralized cortical fibers, 20-40% cancellous chips in a size range of 100-500 μm, and 10-40% carrier.

18. The method of claim 14, wherein the cortico-cancellous chips have a bimodal distribution of 100-500 μm and 500-1500 μm.

19. The method of claim 18, wherein the implantable biomaterial is a crunch including 40-70% demineralized cortical fibers, 10-30% cortico-cancellous chips in a size range of 100-500 μm, 10-30% cortico-cancellous chips in a size range of 500-1500 μm, and 10-40% carrier.

20. The method of claim 14, wherein the condyles and cortical shafts undergo a liquid processing including an antibiotic/antimycotic solution for 10-15 minutes, 0.05-0.15% v/v sodium deoxycholate solution for 15-35 minutes, 2-6% (w/v) hydrogen peroxide solution for 15-35 minutes, and 70% isopropyl alcohol for 5-15 minutes with intermediate rinse steps using sterile water.

* * * * *